(12) United States Patent
Brown et al.

(10) Patent No.: US 11,266,432 B2
(45) Date of Patent: *Mar. 8, 2022

(54) ULTRASONIC SURGICAL INSTRUMENT

(71) Applicant: COVIDIEN LP, Mansfield, MA (US)

(72) Inventors: Michael J. Brown, Superior, CO (US); Jason L. Craig, Loveland, CO (US)

(73) Assignee: Covidien LP, Mansfield, MA (US)

( * ) Notice: Subject to any disclaimer, the term of this patent is extended or adjusted under 35 U.S.C. 154(b) by 298 days.

This patent is subject to a terminal disclaimer.

(21) Appl. No.: 16/521,679

(22) Filed: Jul. 25, 2019

(65) Prior Publication Data

US 2019/0343550 A1 Nov. 14, 2019

Related U.S. Application Data (63) Continuation of application No. 15/496,241, filed on Apr. 25, 2017, now Pat. No. 10,368,898.
(Continued)

(51) Int. Cl.
| | |
|---|---|
| *A61B 17/32* | (2006.01) |
| *A61B 17/00* | (2006.01) |
| *A61B 90/00* | (2016.01) |

(52) U.S. Cl.
CPC ........... *A61B 17/320092* (2013.01); *A61B 17/320068* (2013.01); *A61B 2017/0046* (2013.01);
(Continued)

(58) Field of Classification Search
CPC .... A61B 17/320068; A61B 17/320092; A61B 2017/0046; A61B 2017/00477;
(Continued)

(56) References Cited

U.S. PATENT DOCUMENTS

| | | |
|---|---|---|
| 1,813,902 A | 7/1931 | Bovie |
| 2,235,274 A | 3/1941 | Trehern |

(Continued)

FOREIGN PATENT DOCUMENTS

| | | |
|---|---|---|
| EP | 0705570 A1 | 4/1996 |
| EP | 0908148 A1 | 4/1999 |

(Continued)

OTHER PUBLICATIONS

Extended European Search report issued in corresponding EP application No. 17169447.4 dated Sep. 13, 2017.
(Continued)

*Primary Examiner* — Mohamed G Gabr
(74) *Attorney, Agent, or Firm* — Carter, DeLuca & Farrell LLP (57) ABSTRACT

An ultrasonic surgical instrument includes an elongated assembly releasably engagable with an ultrasonic transducer and including a waveguide having a blade at a distal end and a torque adapter towards a proximal end. Fixed and movable sleeves are disposed about the waveguide and support and operably couple to a jaw member at the respective distal ends thereof. A drive tube is fixed to the movable sleeve such that translation of the drive tube pivots the jaw member relative to the blade. A torque housing is slidably disposed about the drive tube, longitudinally fixed about the fixed sleeve, and fixedly about the torque adapter. A rotation knob is longitudinally fixed about the torque housing and operably coupled to the torque housing such that the torque housing and the rotation knob cooperate to define a torque wrench inhibit application of additional torque to the waveguide above a torque limit.

18 Claims, 10 Drawing Sheets

Related U.S. Application Data (60) Provisional application No. 62/332,028, filed on May 5, 2016.

(52) U.S. Cl.
CPC .............. *A61B 2017/00477* (2013.01); *A61B 2017/00734* (2013.01); *A61B 2017/320052* (2013.01); *A61B 2017/320074* (2017.08); *A61B 2017/320094* (2017.08); *A61B 2090/031* (2016.02); *A61B 2560/0431* (2013.01)

(58) Field of Classification Search
CPC ......... A61B 2017/00734; A61B 2017/320052; A61B 2017/320074; A61B 2017/320094; A61B 2090/031; A61B 2560/0431
See application file for complete search history.

(56) References Cited

U.S. PATENT DOCUMENTS

| | | |
|---|---|---|
| 2,874,470 A | 2/1959 | Richards |
| 2,990,616 A | 7/1961 | Balamuth |
| 3,432,691 A | 3/1969 | Shoh |
| 3,489,930 A | 1/1970 | Shoh |
| 3,526,792 A | 9/1970 | Shoh |
| 3,629,726 A | 12/1971 | Popescu |
| 3,668,486 A | 6/1972 | Silver |
| 3,809,977 A | 5/1974 | Balamuth et al. |
| 3,875,945 A | 4/1975 | Friedman |
| 3,924,335 A | 12/1975 | Balamuth et al. |
| 4,012,647 A | 3/1977 | Balamuth et al. |
| 4,193,818 A | 3/1980 | Young et al. |
| 4,227,110 A | 10/1980 | Douglas et al. |
| 4,300,083 A | 11/1981 | Heiges |
| 4,302,728 A | 11/1981 | Nakamura |
| 4,370,302 A | 1/1983 | Suzuoka et al. |
| 4,641,053 A | 2/1987 | Takeda |
| 5,113,116 A | 5/1992 | Wilson |
| 5,224,680 A | 7/1993 | Greenstein et al. |
| 5,264,925 A | 11/1993 | Shipp et al. |
| 5,275,166 A | 1/1994 | Vaitekunas et al. |
| 5,374,813 A | 12/1994 | Shipp |
| 5,394,187 A | 2/1995 | Shipp |
| 5,408,268 A | 4/1995 | Shipp |
| 5,451,220 A | 9/1995 | Ciervo |
| 5,490,860 A | 2/1996 | Middle et al. |
| 5,565,520 A | 10/1996 | Fock et al. |
| 5,582,617 A | 12/1996 | Klieman et al. |
| 5,593,414 A | 1/1997 | Shipp et al. |
| 5,685,311 A | 11/1997 | Hara |
| 5,717,306 A | 2/1998 | Shipp |
| 5,728,130 A | 3/1998 | Ishikawa et al. |
| 5,776,155 A | 7/1998 | Beaupre et al. |
| 5,792,138 A | 8/1998 | Shipp |
| 5,796,056 A | 8/1998 | Bredow et al. |
| 5,810,859 A | 9/1998 | DiMatteo et al. |
| 5,858,018 A | 1/1999 | Shipp et al. |
| 5,873,873 A | 2/1999 | Smith et al. |
| 5,897,569 A | 4/1999 | Kellogg et al. |
| 5,910,152 A | 6/1999 | Bays |
| 5,938,633 A | 8/1999 | Beaupre |
| 5,944,737 A | 8/1999 | Tsonton et al. |
| 5,947,984 A | 9/1999 | Whipple |
| 5,954,736 A | 9/1999 | Bishop et al. |
| 5,993,465 A | 11/1999 | Shipp et al. |
| 5,994,855 A | 11/1999 | Lundell et al. |
| 6,031,526 A | 2/2000 | Shipp |
| 6,036,667 A | 3/2000 | Manna et al. |
| 6,068,647 A | 5/2000 | Witt et al. |
| 6,095,981 A | 8/2000 | McGahan |
| 6,162,194 A | 12/2000 | Shipp |
| 6,183,426 B1 | 2/2001 | Akisada et al. |
| 6,220,098 B1 | 4/2001 | Johnson et al. |
| 6,254,623 B1 | 7/2001 | Haibel, Jr. et al. |
| 6,257,241 B1 | 7/2001 | Wampler |
| 6,278,218 B1 | 8/2001 | Madan et al. |
| 6,280,407 B1 | 8/2001 | Manna et al. |
| 6,283,981 B1 | 9/2001 | Beaupre |
| 6,284,185 B1 | 9/2001 | Tokuda et al. |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,325,811 B1 | 12/2001 | Messerly |
| 6,328,751 B1 | 12/2001 | Beaupre |
| 6,350,269 B1 | 2/2002 | Shipp et al. |
| 6,352,532 B1 | 3/2002 | Kramer et al. |
| 6,416,486 B1 | 7/2002 | Wampler |
| 6,423,082 B1 | 7/2002 | Houser et al. |
| 6,432,118 B1 | 8/2002 | Messerly |
| 6,443,968 B1 | 9/2002 | Holthaus et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,482,220 B1 | 11/2002 | Mueller |
| 6,491,708 B2 | 12/2002 | Madan et al. |
| 6,500,188 B2 | 12/2002 | Harper et al. |
| 6,514,267 B2 | 2/2003 | Jewett |
| 6,537,291 B2 | 3/2003 | Friedman et al. |
| 6,561,983 B2 | 5/2003 | Cronin et al. |
| 6,565,520 B1 | 5/2003 | Young |
| 6,588,277 B2 | 7/2003 | Giordano et al. |
| 6,589,200 B1 | 7/2003 | Schwemberger et al. |
| 6,607,540 B1 | 8/2003 | Shipp |
| 6,623,500 B1 | 9/2003 | Cook et al. |
| 6,626,926 B2 | 9/2003 | Friedman et al. |
| 6,633,234 B2 | 10/2003 | Wiener et al. |
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,678,621 B2 | 1/2004 | Wiener et al. |
| 6,679,899 B2 | 1/2004 | Wiener et al. |
| 6,719,776 B2 | 4/2004 | Baxter et al. |
| 6,752,815 B2 | 6/2004 | Beaupre |
| 6,773,444 B2 | 8/2004 | Messerly |
| 6,869,439 B2 | 3/2005 | White et al. |
| 6,908,472 B2 | 6/2005 | Wiener et al. |
| 6,915,623 B2 | 7/2005 | Dey et al. |
| 6,945,981 B2 | 9/2005 | Donofrio et al. |
| 6,976,969 B2 | 12/2005 | Messerly |
| 7,037,306 B2 | 5/2006 | Podany et al. |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger et al. |
| 7,163,548 B2 | 1/2007 | Stulen et al. |
| 7,179,254 B2 | 2/2007 | Pendekanti et al. |
| 7,179,271 B2 | 2/2007 | Friedman et al. |
| 7,207,997 B2 | 4/2007 | Shipp et al. |
| 7,217,128 B2 | 5/2007 | Atkin et al. |
| 7,217,893 B1 | 5/2007 | Huang et al. |
| 7,230,199 B2 | 6/2007 | Chou et al. |
| 7,244,262 B2 | 7/2007 | Wiener et al. |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 7,977,587 B2 | 7/2011 | Rajagopal et al. |
| 8,435,258 B2 | 5/2013 | Young et al. |
| 8,672,959 B2 | 3/2014 | Witt et al. |
| 10,368,898 B2 * | 8/2019 | Brown ........... A61B 17/320092 |
| 2001/0048855 A1 | 12/2001 | Lin |
| 2002/0002379 A1 | 1/2002 | Bishop |
| 2002/0077645 A1 | 6/2002 | Wiener et al. |
| 2002/0091339 A1 | 7/2002 | Horzewski et al. |
| 2003/0144680 A1 | 7/2003 | Kellogg et al. |
| 2003/0149424 A1 | 8/2003 | Barlev et al. |
| 2003/0199794 A1 | 10/2003 | Sakurai et al. |

(56) References Cited

U.S. PATENT DOCUMENTS

| | | |
|---|---|---|
| 2003/0212363 A1 | 11/2003 | Shipp |
| 2004/0097972 A1 | 5/2004 | Shipp et al. |
| 2004/0116952 A1 | 6/2004 | Sakurai et al. |
| 2004/0256487 A1 | 12/2004 | Collins et al. |
| 2005/0091770 A1 | 5/2005 | Mourad et al. |
| 2005/0107658 A1 | 5/2005 | Brockway |
| 2005/0113815 A1 | 5/2005 | Ritchie et al. |
| 2005/0119677 A1 | 6/2005 | Shipp |
| 2005/0149063 A1 | 7/2005 | Young et al. |
| 2005/0203329 A1 | 9/2005 | Muto et al. |
| 2005/0234338 A1 | 10/2005 | Masuda |
| 2005/0234484 A1 | 10/2005 | Houser et al. |
| 2006/0058825 A1 | 3/2006 | Ogura et al. |
| 2006/0079878 A1 | 4/2006 | Houser |
| 2006/0079879 A1 | 4/2006 | Faller et al. |
| 2006/0087286 A1 | 4/2006 | Phillips et al. |
| 2006/0129168 A1 | 6/2006 | Shipp |
| 2006/0178579 A1 | 8/2006 | Haynes |
| 2006/0178667 A1 | 8/2006 | Sartor et al. |
| 2006/0194567 A1 | 8/2006 | Kelly et al. |
| 2006/0206100 A1 | 9/2006 | Eskridge et al. |
| 2006/0217729 A1 | 9/2006 | Eskridge et al. |
| 2007/0011836 A1 | 1/2007 | Brewer et al. |
| 2007/0149881 A1 | 6/2007 | Rabin |
| 2007/0166663 A1 | 7/2007 | Telles et al. |
| 2007/0175960 A1 | 8/2007 | Shelton et al. |
| 2007/0227866 A1 | 10/2007 | Dimig |
| 2007/0239028 A1 | 10/2007 | Houser et al. |
| 2007/0239101 A1 | 10/2007 | Kellogg |
| 2007/0282333 A1 | 12/2007 | Fortson et al. |
| 2008/0033248 A1 | 2/2008 | Akagi |
| 2008/0051693 A1 | 2/2008 | Babaev |
| 2008/0245841 A1 | 10/2008 | Smith et al. |
| 2009/0138006 A1 | 5/2009 | Bales et al. |
| 2009/0143797 A1 | 6/2009 | Smith et al. |
| 2009/0143805 A1 | 6/2009 | Palmer et al. |
| 2009/0223033 A1 | 9/2009 | Houser |
| 2010/0004669 A1 | 1/2010 | Smith et al. |
| 2010/0090420 A1 | 4/2010 | Nickels, Jr. et al. |
| 2012/0078278 A1 | 3/2012 | Bales, Jr. et al. |
| 2013/0338691 A1 | 12/2013 | Young et al. |
| 2014/0107684 A1 | 4/2014 | Craig |
| 2015/0148830 A1 | 5/2015 | Stulen et al. |
| 2015/0245850 A1* | 9/2015 | Hibner ........... A61B 17/320092 606/171 |

FOREIGN PATENT DOCUMENTS

| | | |
|---|---|---|
| EP | 1594209 A1 | 11/2005 |
| EP | 1707131 A1 | 10/2006 |
| EP | 2200145 A1 | 6/2010 |
| EP | 2510891 A1 | 10/2012 |
| JP | 2000506430 A | 5/2000 |
| JP | 2001112768 A | 4/2001 |
| JP | 2001514541 A | 9/2001 |
| JP | 2002518067 A | 6/2002 |
| JP | 2003502102 A | 1/2003 |
| JP | 2003285008 A | 10/2003 |
| JP | 2004129871 A | 4/2004 |
| JP | 2005278932 A | 10/2005 |
| JP | 2005296411 A | 10/2005 |
| JP | 2009538710 A | 11/2009 |
| WO | 2006087885 A1 | 8/2006 |
| WO | 2006119376 A2 | 11/2006 |
| WO | 2007047380 A2 | 4/2007 |
| WO | 2007080723 A1 | 7/2007 |

OTHER PUBLICATIONS

Japanese Office Action issued in corresponding JP application No. 2017-091567 dated Mar. 12, 2018, including English translation, 12 pages.

European Examination Report issued in corresponding European Application No. 17169447.4 dated Sep. 4, 2019, 6 pages.

* cited by examiner

ULTRASONIC SURGICAL INSTRUMENT

CROSS REFERENCE TO RELATED APPLICATION

The present application is a continuation of U.S. patent application Ser. No. 15/496,241, filed on Apr. 25, 2017, which claims the benefit of and priority to U.S. Provisional Patent Application No. 62/332,028, filed on May 5, 2016, the entire contents of each of which are incorporated herein by reference.

BACKGROUND

Technical Field

The present disclosure relates to surgical instruments and, more particularly, to an ultrasonic surgical instrument configured to treat tissue with ultrasonic energy.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, fulgurate, or otherwise treat tissue.

Typically, an ultrasonic surgical instrument is configured to transmit ultrasonic energy produced by a generator and transducer assembly along a waveguide to an end effector that is spaced-apart from the generator and transducer assembly. With respect to cordless ultrasonic instruments, for example, a portable power source, e.g., a battery, and the generator and transducer assembly are mounted on the handheld instrument itself, while the waveguide interconnects the generator and transducer assembly and the end effector. Wired ultrasonic instruments operate in similar fashion except that, rather than having the generator and power source mounted on the handheld instrument itself, the handheld instrument is configured to connect to a standalone power supply and/or generator via a wired connection.

Regardless of the particular type and/or configuration of ultrasonic surgical instrument utilized, it is important to ensure proper engagement between the transducer and waveguide so that the ultrasonic energy is properly transmitted to the end effector for treating tissue therewith.

SUMMARY

As used herein, the term "distal" refers to the portion that is being described which is further from a user, while the term "proximal" refers to the portion that is being described which is closer to a user. Further, to the extent consistent any or all of the aspects detailed herein may be used in conjunction with any or all of the other aspects detailed herein.

In accordance with aspects of the present disclosure, an elongated assembly configured to releasably engage an ultrasonic transducer of an ultrasonic surgical instrument is provided including a waveguide, a fixed sleeve and a movable sleeve, a jaw member, a drive assembly, a torque housing, and a rotation knob. The waveguide defines a blade at a distal end, an engagement member at a proximal end, and includes a torque adapter fixedly engaged thereabout towards the proximal end. The fixed and movable sleeves are disposed about the waveguide and each define a proximal end and a distal end. The jaw member is pivotably supported at the distal end of the fixed sleeve and operably coupled to the movable sleeve such that translation of the movable sleeve relative to the fixed sleeve pivots the jaw members relative to the blade between an open position and a clamping position. The drive assembly includes a drive tube longitudinally fixed about the proximal end of the movable sleeve and slidably disposed about the fixed sleeve such that translation of the drive tube pivots the jaw member between the open position and the clamping position. The drive tube slidably receives the torque adapter therethrough. The torque housing is slidably disposed about the drive tube, longitudinally fixed about the proximal end of the fixed sleeve, and fixedly engaged about the torque adapter. The rotation knob is longitudinally fixed about the torque housing and operably coupled to the torque housing such that the torque housing and the rotation knob cooperate to define a torque wrench configured to inhibit application of additional torque to the waveguide above a torque limit.

In aspects of the present disclosure, the torque housing includes at least one cantilever arm extending outwardly therefrom and the rotation knob defines a plurality of spaced-apart channels disposed radially about an annular interior surface thereof. In such aspects, each of the at least one cantilever arms is configured for receipt within one of the plurality of spaced-apart channels to impart rotation to the waveguide in response to rotation of the rotation knob up to the torque limit. Each of the at least one cantilever arms is further configured to cam out of the one of the plurality of spaced-apart channels to decouple the rotation knob from the torque housing to inhibit application of additional torque to the waveguide above the torque limit.

In aspects of the present disclosure, the fixed sleeve defines a proximal collar at the proximal end thereof and the torque housing defines an annular channel configured to receive the proximal collar of the fixed sleeve to longitudinally fix the torque housing about the proximal end of the fixed sleeve. Additionally or alternatively, the movable sleeve may define a proximal collar at the proximal end thereof and the drive tube may be configured to engage the proximal collar of the movable sleeve to longitudinally fix the drive tube about the proximal end of the movable sleeve.

In aspects of the present disclosure, the movable sleeve is coaxially disposed about the fixed sleeve.

In aspects of the present disclosure, the torque housing includes first and second housing parts configured to engage one another via snap-fitting to form the torque housing.

In aspects of the present disclosure, the torque housing defines a receiver block configured to receive the torque adapter to fixedly engage the torque adapter and, thus, the waveguide relative to the torque housing.

In aspects of the present disclosure, the drive assembly further includes a collar fixedly engaged about the drive tube towards a proximal end thereof, a washer fixed engaged about the drive tube towards a distal end thereof, a ferrule slidably disposed about the drive tube between the washer and the collar, and a biasing member disposed about the drive tube between the washer and the ferrule so as to bias the ferrule proximally.

In aspects of the present disclosure, the drive assembly is configured such that urging the ferrule proximally urges the drive tube proximally to pivot the jaw member from the open position to the clamping position to grasp tissue therebetween up to a clamping pressure limit, and such that further proximal urging of the ferrule compresses the biasing member while maintaining the drive tube in position to inhibit application of additional clamping pressure above the clamping pressure limit.

In aspects of the present disclosure, the ferrule and the collar define an annular gap therebetween that is configured to receive a driving portion of a movable handle for urging the ferrule proximally.

In accordance with aspects of the present disclosure, an ultrasonic surgical instrument is provided including a handle assembly and an elongated assembly configured to releasably engage the handle assembly. The handle assembly includes a housing, an ultrasonic transducer coupled to the housing and including a horn having a first engagement member disposed at a free end thereof, and a movable handle pivotably coupled to the housing and including a grasping portion extending from the housing and a driving portion extending into the housing. The elongated assembly may be configured similarly to any or all of the aspects detailed above or otherwise herein.

In aspects of the present disclosure, a generator is engaged with the ultrasonic transducer to define a transducer and generator assembly that is configured to releasably couple to the housing.

In aspects of the present disclosure, a battery assembly is configured to releasably couple to the housing to power the generator for driving the ultrasonic transducer.

In aspects of the present disclosure, with the elongated assembly engaged with the handle assembly, the proximal end of the waveguide, at least a portion of the drive assembly, and at least a portion of the torque housing extend into the housing, while the rotation knob is disposed distally adjacent the housing.

In aspects of the present disclosure, with the elongated assembly engaged with the handle assembly, the driving portion of the movable handle is engaged within the drive assembly such that actuation of the movable handle urges the ferrule proximally to thereby urge the drive tube proximally to pivot the jaw member from the open position to the clamping position to grasp tissue therebetween up to a clamping pressure limit, and such that further actuation of the movable handle urges the ferrule further proximally to compress the biasing member while maintaining the drive tube in position to inhibit application of additional clamping pressure above the clamping pressure limit.

In aspects of the present disclosure, with the elongated assembly engaged with the handle assembly, rotation of the rotation knob rotates the elongated assembly and the ultrasonic transducer relative to the housing.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements and.

DETAILED DESCRIPTION

Figure 1:
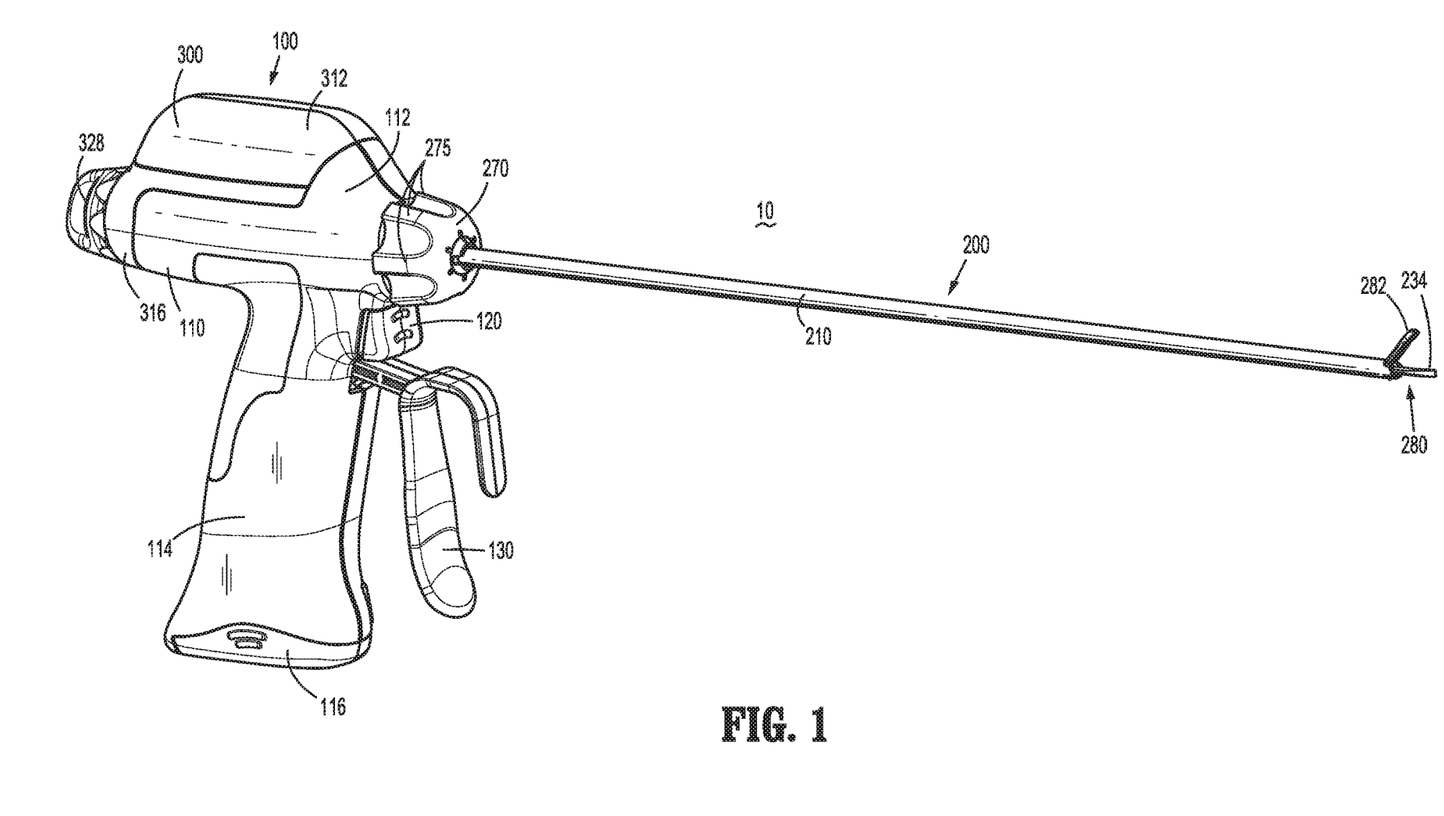
FIG. 1 is a perspective view of an ultrasonic surgical instrument provided in accordance with the present disclosure.
Figure 2:
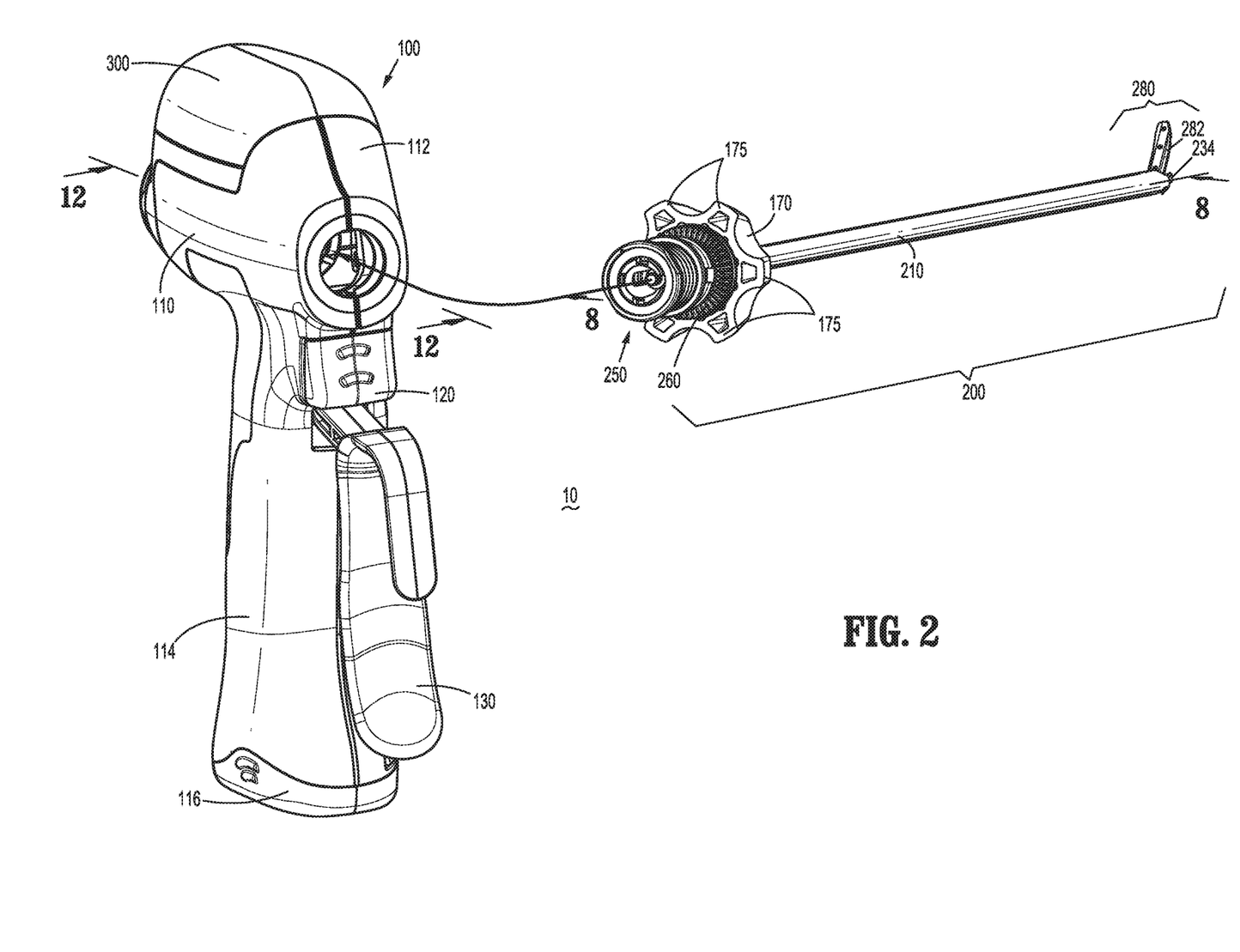
FIG. 2 is a perspective view of the ultrasonic surgical instrument of FIG. 1 with the elongated assembly separated from the handle assembly.
Figure 3:
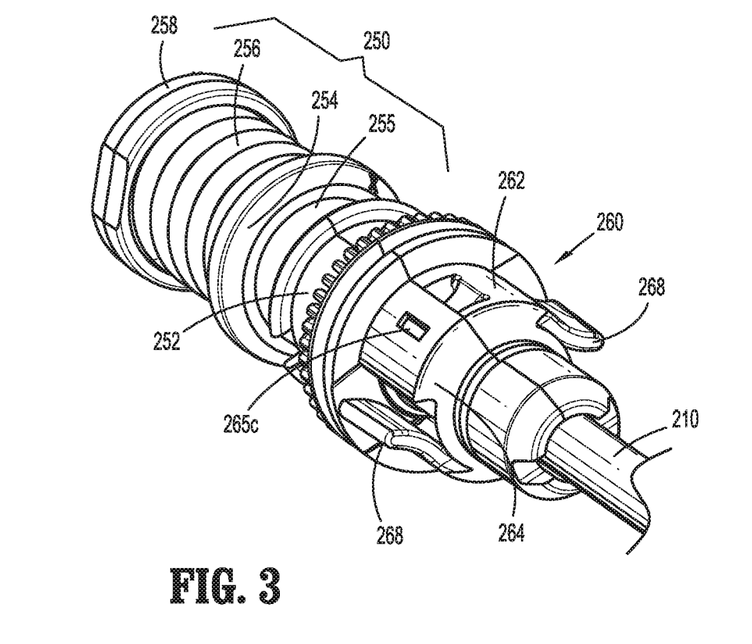
FIG. 3 is a front, perspective view of the proximal end of the elongated assembly of FIG. 2, with parts removed.
Figure 4:
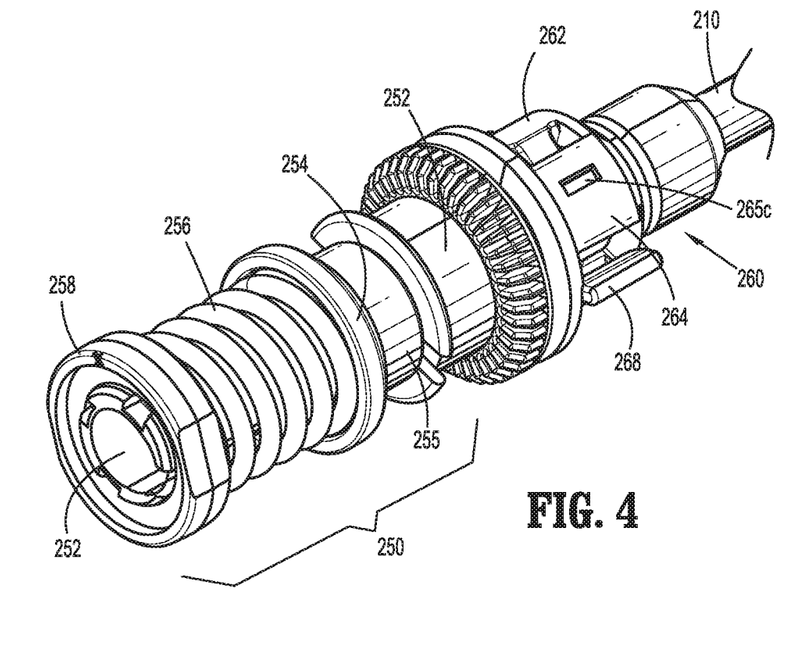
FIG. 4 is a rear, perspective view of the proximal end of the elongated assembly of FIG. 2, with parts removed.

Referring generally to FIGS. 1 and 2, an ultrasonic surgical instrument provided in accordance with the aspects and features of the present disclosure is shown generally identified by reference numeral 10. Ultrasonic surgical instrument 10 generally includes a handle assembly 100 and an elongated assembly 200 that is configured to releasably engage handle assembly 100. Handle assembly 100 includes a housing 110 defining a body portion 112 configured to support an ultrasonic transducer and generator assembly ("TAG") 300, and a fixed handle portion 114 defining a compartment 116 configured to receive a battery assembly 400. Handle assembly 100 further includes an activation button 120 operably positioned to electrically couple between TAG 300 and battery assembly 400 when TAG 300 is mounted on body portion 112 of housing 110 and battery assembly 400 is engaged within compartment 116 of housing 110.

A clamp trigger 130 extends from housing 110 of handle assembly 100 adjacent fixed handle portion 114 of housing 110. Clamp trigger 130 includes a bifurcated drive portion 132 extending into body portion 112 of housing 110 and is selectively movable relative to housing 110 to actuate ultrasonic surgical instrument 10, as detailed below.

TAG 300 and battery assembly 400, as noted above, are each removable from handle assembly 100 to facilitate disposal of handle assembly 100 after a single use or to enable sterilization of handle assembly 100 for subsequent use. TAG 300 may be configured to withstand sterilization such that TAG 300 may be sterilized for repeated use. Battery assembly 400, on the other hand, is configured to be aseptically transferred and retained within compartment 116 of fixed handle portion 114 of housing 110 of handle assembly 100 such that battery assembly 400 may be repeatedly used without requiring sterilization thereof.

Figure 12:
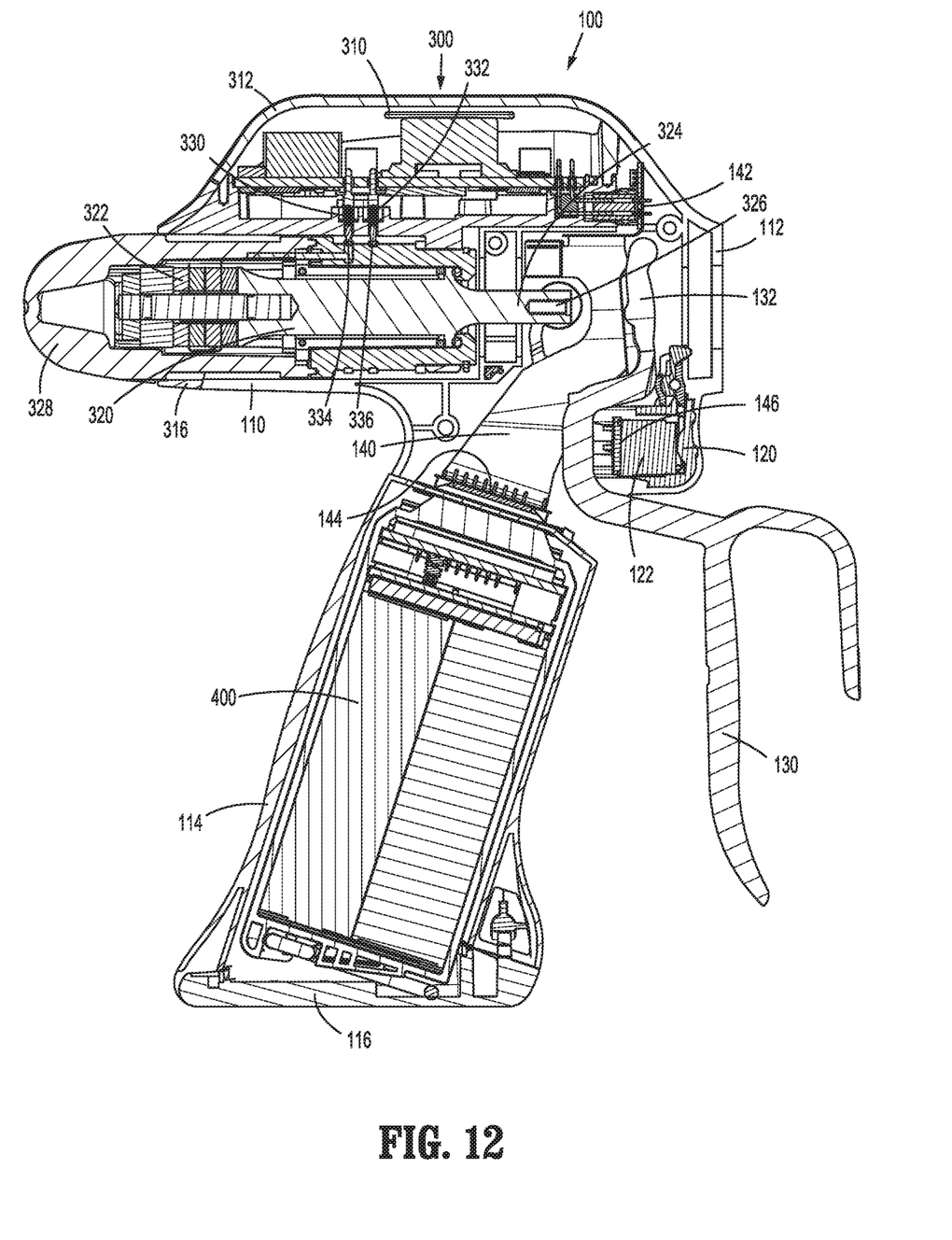
FIG. 12 is a longitudinal, cross-sectional view taken across section line "12-12" of FIG. 2.

With additional reference to FIGS. 12, an electrical connector 140 disposed within housing 110 of handle assembly 100 includes TAG contacts 142, battery assembly contacts 144, and an activation button connector 146. Electrical connector 140 electrically couples to activation button 120 via activation button connector 146, is configured to electrically couple to TAG 300 via TAG contacts 142 upon engagement of TAG 300 with body portion 112 of housing 110 of handle assembly 100, and is configured to electrically couple to battery assembly 400 via battery assembly contacts 144 upon engagement of battery assembly 400 within compartment 116 of fixed handle portion 114 of housing 110 of handle assembly 100. As such, in use, when activation button 120 is activated in an appropriate manner, an underlying two-mode switch assembly 122 is activated to supply power from battery assembly 400 to TAG 300 in either a "LOW" power mode or a "HIGH" power mode, depending upon the manner of activation of activation button 120.

Continuing with reference to FIGS. 1, 2, and 12, TAG 300 includes a generator 310 and an ultrasonic transducer 320. Generator 310 includes a housing 312 configured to house the internal electronics of generator 310, and a cradle 314 configured to rotatably support ultrasonic transducer 320. Ultrasonic transducer 320 includes a piezoelectric stack 322 and a distally-extending horn 324. Horn 324 defines a threaded female receiver 326 at the free distal end thereof. A set of connectors 330, 332 and corresponding rotational contacts 334, 336 associated with generator 310 and ultrasonic transducer 320, respectively, enable drive signals to be communicated from generator 310 to piezoelectric sack 322 to drive ultrasonic transducer 320. More specifically, piezoelectric stack 322 of ultrasonic transducer 320 converts a high voltage AC signal received from generator 310 into mechanical motion that is output from horn 324 to elongated assembly 200, as detailed below. Ultrasonic transducer 320 further includes a rotation knob 328 disposed at a proximal end thereof to enable rotation of ultrasonic transducer 320 relative to generator 310, the importance of which is detailed below.

Referring to FIGS. 2-11, elongated assembly 200 includes an outer drive sleeve 210, an inner support sleeve 220 disposed within outer drive sleeve 210 and about which outer drive sleeve 210 is configured to slide, a waveguide 230 extending through inner support sleeve 220, a torque adapter 240 engaged about waveguide 230, a drive assembly 250 disposed about outer drive sleeve 210 and operably coupled between outer drive sleeve 210 and bifurcated drive portion 132 of clamp trigger 130 (FIG. 13), a torque housing 260 disposed about outer drive sleeve 210 and operably coupled to waveguide 230, a rotation knob 270 operably disposed about torque housing 260, and an end effector 280 disposed at the distal end of inner support sleeve 220. Elongated assembly 200, as detailed below, is configured to releasably engage handle assembly 100 such that mechanical motion output from horn 324 of ultrasonic transducer 320 (see FIG. 12) is transmitted along waveguide 230 to end effector 280 for treating tissue therewith, such that clamp trigger 130 (FIG. 13) is selectively actuatable to manipulate end effector 280, and such that rotation knob 270 is selectively rotatable to rotate elongated assembly 200 relative to handle assembly 100. Elongated assembly 200 may be configured as a disposable, single-use component or a reusable component that is sterilizable for subsequent use.

Figure 5:
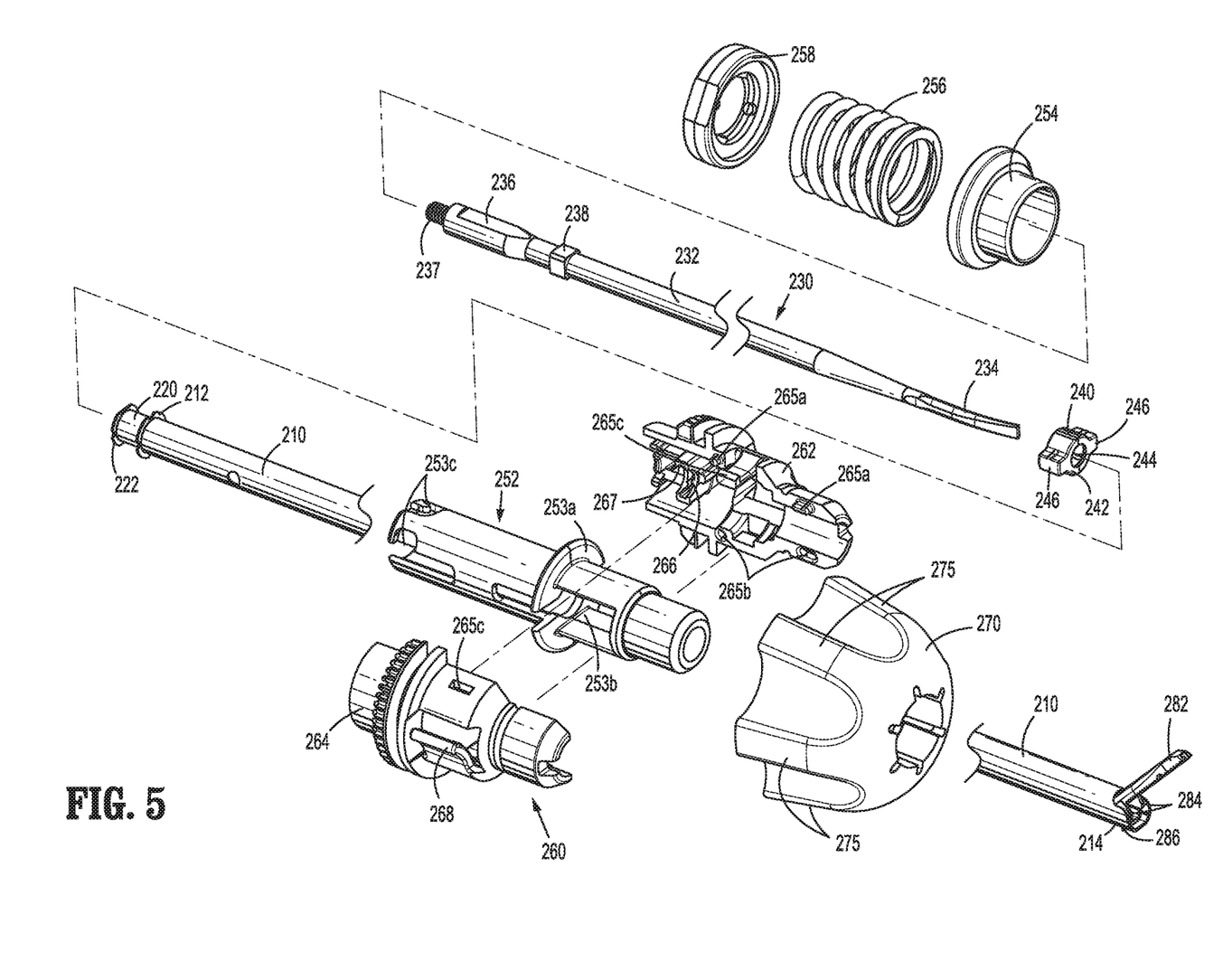
FIG. 5 is an exploded, perspective view of the elongated assembly of FIG. 2.
Figure 6:
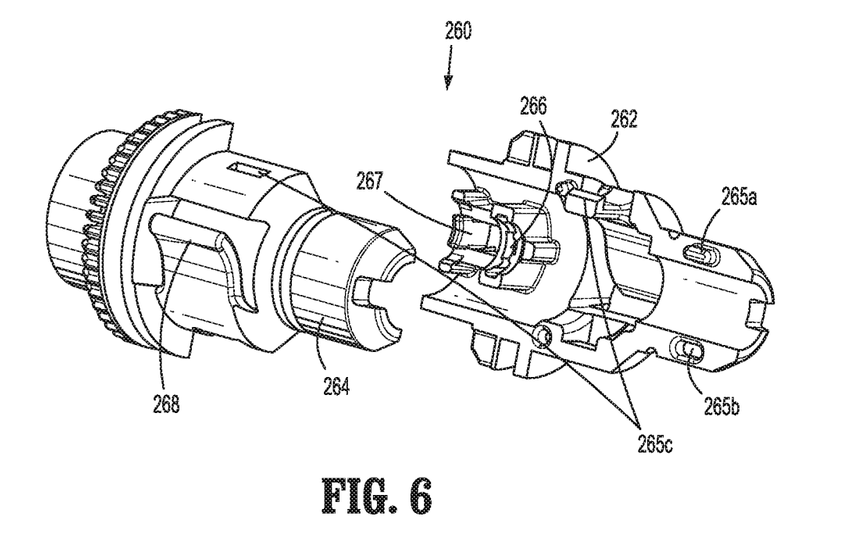
FIG. 6 is an exploded, perspective view of the torque housing of the elongated assembly of FIG. 2.
Figure 7:
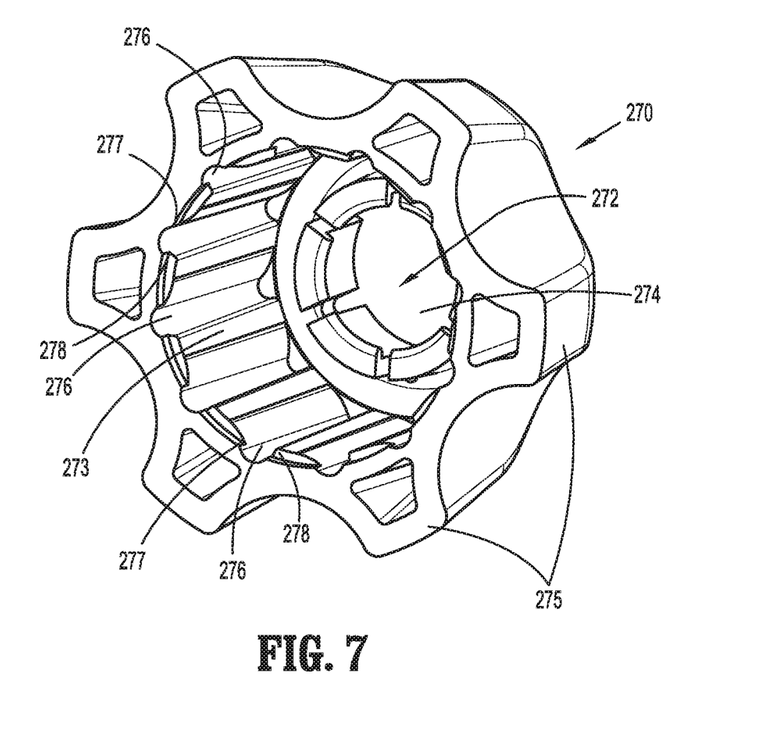
FIG. 7 is a perspective view of the rotation knob of the elongated assembly of FIG. 2.
Figure 8:
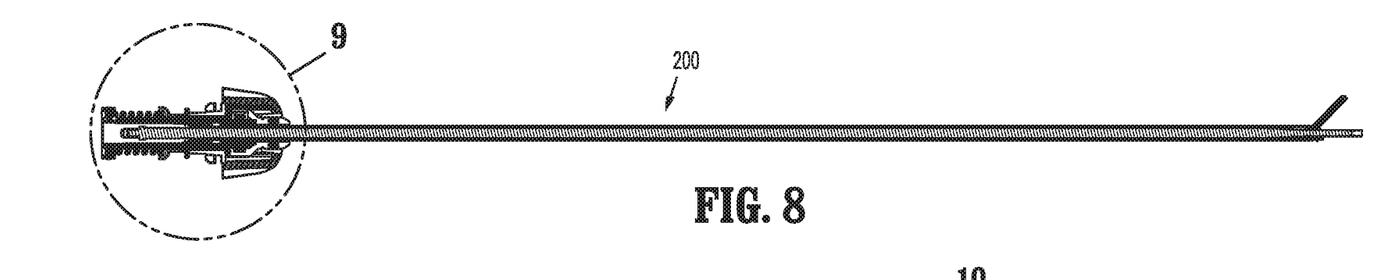
FIG. 8 is a longitudinal, cross-sectional view taken across section line "8-8" of FIG. 2.
Figure 9:
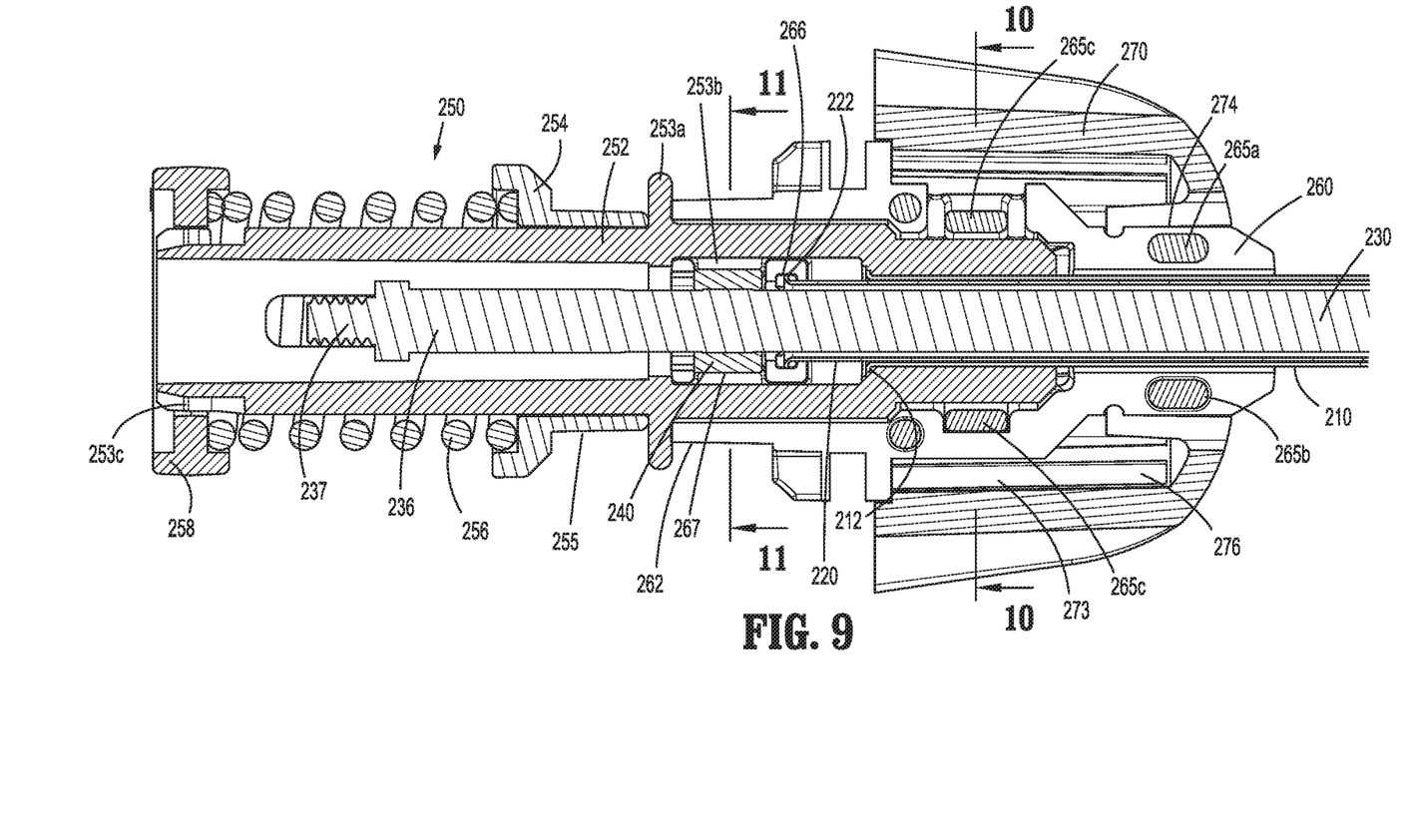
FIG. 9 is an enlarged view of the area of detail indicated as "9" in FIG. 8.
Figure 10:
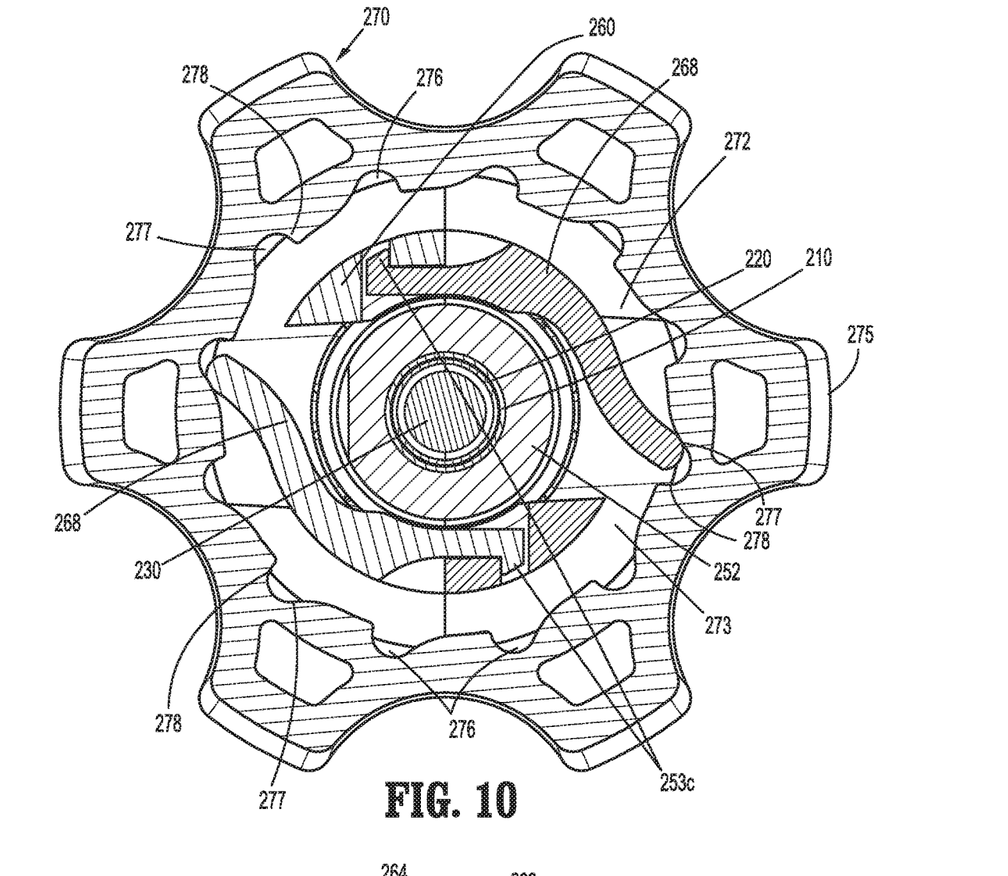
FIG. 10 is a transverse, cross-sectional view taken across section line "10-10" of FIG. 9.
Figure 11:
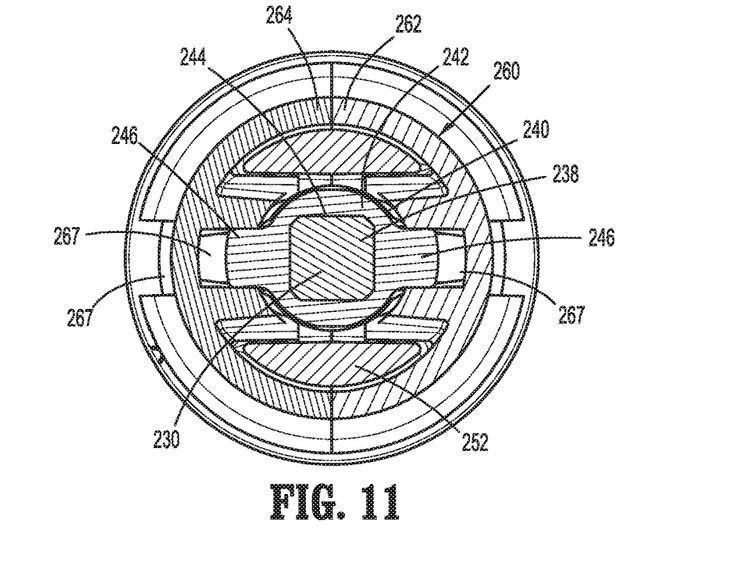
FIG. 11 is a transverse, cross-sectional view taken across section line "11-11" of FIG. 9.

Referring to FIGS. 5, 8, and 9, outer drive sleeve 210, as noted above, is slidably disposed about inner support sleeve 220. Outer drive sleeve 210, as detailed below, is fixed relative to drive tube 252 of drive assembly 250. Outer drive sleeve 210 and inner support sleeve 220 each include a proximal collar 212, 222, respectively, defined at the proximal end thereof, and each is operably coupled to jaw member 282 of end effector 280 at the distal end thereof. More specifically, jaw member 282 includes a pair of jaw flanges 284 that are pivotably mounted at the distal end of inner support sleeve 220 to pivotably couple jaw member 282 to inner support sleeve 220, and a jaw foot 286 extending through an aperture 214 defined within outer drive sleeve 210 at the distal end thereof such that proximal translation outer drive sleeve 210 about inner support sleeve 220 and relative to end effector 280 pivots jaw member 282 from an open position to a clamping position.

Figure 13:
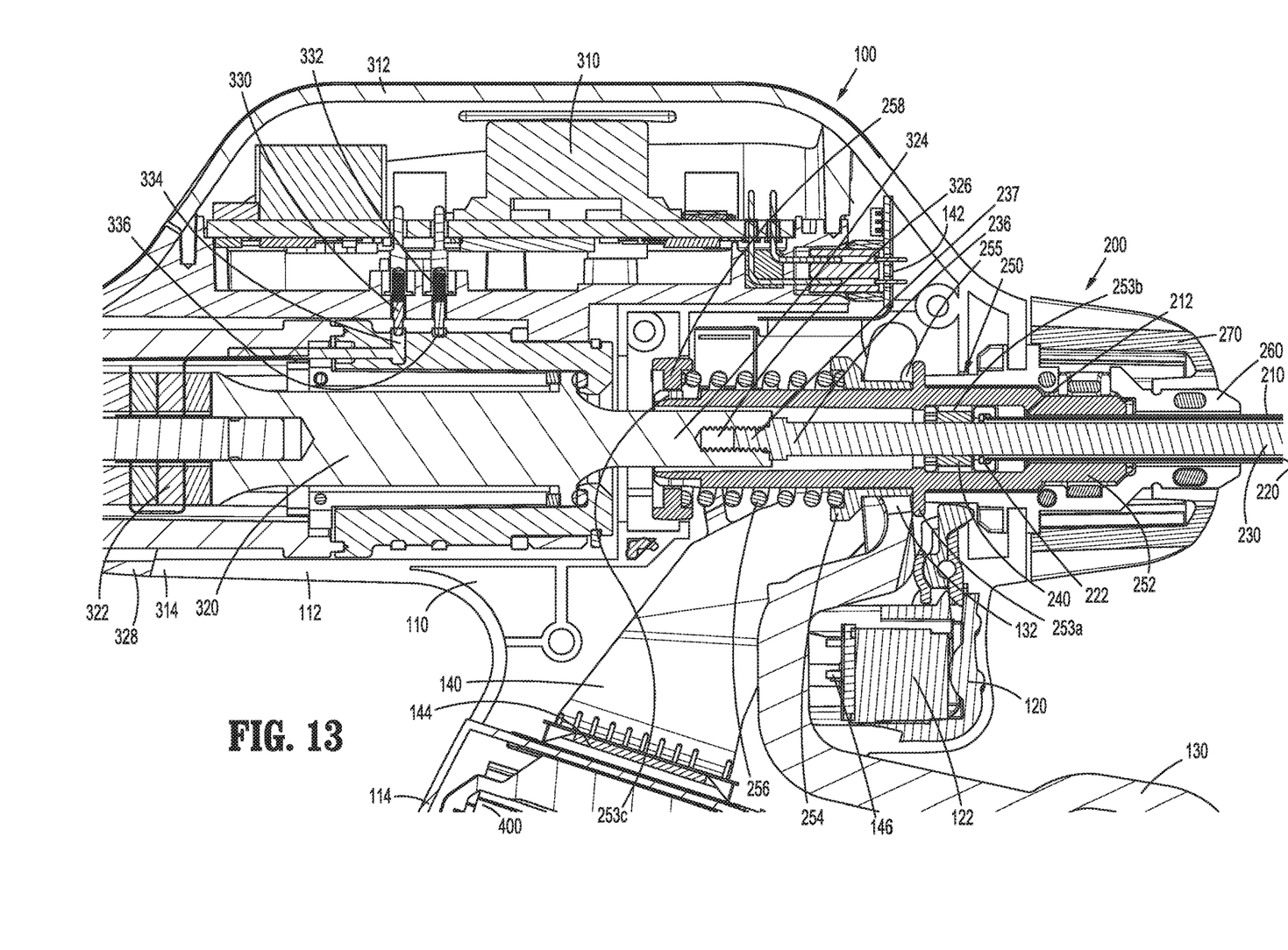
FIG. 13 is an enlarged, longitudinal, cross-sectional view of a portion of the ultrasonic surgical instrument of FIG. 1 illustrating engagement between the elongated assembly and the handle assembly.

With additional reference to FIG. 13, waveguide 230, as noted above, extends through inner support sleeve 220. Waveguide 230 defines a body 232, a blade 234 extending from the distal end of body 232, a proximal connector 236 extending from the proximal end of body 232, and a seat 238 defined about body 232 towards the proximal end thereof. Blade 234 extends distally from inner support sleeve 220 and forms part of end effector 280 in that blade 234 is positioned to oppose jaw member 282 such that pivoting of jaw member 282 from the open position to the clamping position enables clamping of tissue between jaw member 282 and blade 234. Blade 234 defines a curved configuration wherein the directions of movement of jaw member 282 between the open and clamping positions are perpendicular to the direction of curvature of blade 234. However, it is also contemplated that blade 234 define a straight configuration or that blade 234 curve towards or away from jaw member 282, that is, where the directions of movement of jaw member 282 between the open and clamping positions are coaxial or parallel to the direction of curvature of blade 234.

Proximal connector 236 of waveguide 230 is configured to enable engagement of waveguide 230 with horn 324 of ultrasonic transducer 320 such that mechanical motion produced by ultrasonic transducer 320 is capable of being transmitted along waveguide 230 to blade 234 for treating tissue clamping between blade 234 and jaw member 282 or positioned adjacent to blade 234. To this end, proximal connector 236 includes a threaded male shaft 237 that is configured for threaded engagement within threaded female receiver 326 of horn 324 of ultrasonic transducer 320. As can be appreciated, it is important to ensure that waveguide 230 and ultrasonic transducer 320 are sufficiently engaged with one another and also important to inhibit over-tightening of the engagement between threaded male shaft 237 and threaded female receiver 326. As detailed below, torque housing 260 helps ensure that waveguide 230 and ultrasonic transducer 320 are sufficiently engaged while inhibiting over-tightening.

Referring to FIGS. 5, 6, 9, and 11, torque adapter 240, as noted above, is engaged about waveguide 230. More specifically, torque adapter 240 defines a body 242 having a rectangular-shaped throughbore 244 that receives seat 238 of waveguide 230. Seat 238 defines a rectangular configuration having flat surfaces to rotationally lock torque adapter 240 about waveguide 230. Torque adapter 240 may be overmolded about seat 238. Alternatively, torque adapter 240 may be slid proximally over blade 234 of waveguide 230, body 232 of waveguide 230, and into position about seat 238 of waveguide 230 and secured thereto via welding, press-fitting, or in any other suitable fashion. Torque adapter 240 further defines a pair of wings 246 extending outwardly from opposite sides thereof. Wings 246, as detailed below, are configured to enable rotational locking of torque adapter 240 and, thus, waveguide 230, relative to outer drive sleeve 210, inner support sleeve 220, drive assembly 250, torque housing 260, and rotation knob 270 such that these components rotate together relative to handle assembly 100 upon manipulation of rotation knob 270.

Turning to FIGS. 2-5, 9, and 13, drive assembly 250 is disposed about outer drive sleeve 210 and operably coupled between outer drive sleeve 210 and bifurcated drive portion 132 of clamp trigger 130. Drive assembly 250 includes a drive tube 252 and a ferrule 254, a biasing member 256 (e.g., a spring), and a washer 258, all of which are disposed about drive tube 252. Drive tube 252 defines a raised collar 253a, a pair of opposed slots 253b, and a proximal keying feature 253c. Opposed slots 253b are configured to receive wings 246 of torque adapter 240 therethrough and are elongated relative to wings 246 such that drive tube 252 is capable of being slid about and relative to torque adapter 240, e.g., to open and clamp jaw member 282 relative to blade 234.

Ferrule 254 is slidably disposed about drive tube 252 proximally of raised collar 253a such that raised collar 253a provides a distal stop for ferrule 254. An annular gap 255 defined between the proximal end of ferrule 254 and raised collar 253a of drive tube 252 is configured to receive bifurcated drive portion 132 of clamp trigger 130 (FIG. 13) on either side thereof such that actuation of clamp trigger 130 urges ferrule 254 proximally about and relative to drive tube 252.

Biasing member 256 is disposed about drive tube 252 and is positioned proximally of ferrule 254, while washer 258 is engaged about the proximal end of drive tube 252 via proximal keying feature 253c so as to retain biasing member 256 between washer 258 and ferrule 254. Biasing member 256 is retained in a pre-compressed condition and is configured to bias ferrule 254 into abutment with raised collar 253a of drive tube 252.

Referring to FIGS. 5, 8, 9, and 13, drive tube 252 is configured to slidably receive the proximal end of inner support sleeve 220 and to fixedly engage proximal collar 212 of outer drive sleeve 210 therein such that sliding of drive tube 252 about inner support sleeve 220 likewise slides outer drive sleeve 210 about inner support sleeve 220. As noted above, outer drive sleeve 210 is operably coupled to jaw member 282 of end effector 280 such that proximal translation of outer drive sleeve 210 pivots jaw member 282 from the open position to the clamping position.

The above-detailed configuration of drive assembly 250 provides a force-limiting feature whereby, during initial actuation of clamp trigger 130, biasing member 256 resists compression such that ferrule 254, biasing member 256, washer 258, drive tube 252, and outer drive sleeve 210 are together moved proximally to pivot jaw member 282 from the open position towards the clamping position. However, upon clamping of tissue between jaw member 282 and blade 234 under sufficient clamping pressure so as to overcome the bias of biasing member 256, further actuation of clamp trigger 130 results in further proximal movement of ferrule 254 and compression of biasing member 256 such that washer 258, drive tube 252, and outer drive sleeve 210 are not moved further proximally. As such, further clamping pressure is inhibited from being applied to tissue grasped between jaw member 282 and blade 232. Biasing member 256 may be configured to limit the clamping pressure to a particular clamping pressure or a clamping pressure within a particular clamping pressure range.

With reference to FIGS. 3-6 and 9-11, torque housing 260, as noted above, is disposed about drive tube 252 and operably coupled to waveguide 230. Torque housing 260 is formed from first and second housing parts 262, 264 that each include respective alignment posts 265a and alignment apertures 265b as well as snap-fit features 265c to enable alignment and snap-fit engagement of first and second housing parts 262, 264 to one another to form torque housing 260 about drive tube 252. Torque housing 260 further includes an annular channel 266 (a portion of which is defined on the interior of each of first and second housing parts 262, 264), a receiver block 267 (a portion of which is defined within the interior of each of first and second housing parts 262, 264), and a pair cantilever arms 268 (one disposed on and extending outwardly from each of first and second housing parts 262, 264). Torque housing 260 is configured for positioning about drive tube 252 distally of ferrule 254 such that drive tube 252 is permitted to slide through and relative to torque housing 260.

Annular channel 266 of torque housing 260 is configured to receive proximal collar 222 of inner support sleeve 220 to thereby longitudinally fix torque housing 260 and inner support sleeve 220 relative to one another. Annular channel 266 and/or proximal collar 222 may further include rotational lock features (not explicitly shown) configured to rotationally fix torque housing 260 and inner support sleeve 220 relative to one another.

Receiver block 267 is complementary to and configured to receive wings 246 of torque adapter 240 to longitudinally and rotationally lock torque housing 260 relative to torque adapter 240 and, thus, waveguide 230.

Cantilever arms 268 are configured, in conjunction with rotation knob 270, to serve as a torque-wrench that ensures appropriate application of torque to sufficiently engage waveguide 230 and ultrasonic transducer 320 to one another during assembly, while inhibiting over-tightening of the engagement between waveguide 230 and ultrasonic transducer 320, as detailed below.

Referring to FIGS. 5, 7, 10, and 14, rotation knob 270 defines a lumen 272 therethrough having a proximal portion 273 of a first diameter and distal portion 274 of a second, smaller diameter. Rotation knob 270 further defines a plurality of flutes 275 annularly disposed about the exterior thereof to facilitate grasping and rotating rotation knob 270. Rotation knob 270 is configured for positioning about torque housing 260 such that cantilever arms 268 are disposed within the proximal portion 273 of lumen 272. The distal portion 274 of lumen 272 of rotation knob 270 is configured for receipt about the distal end of torque housing 260 in longitudinally-fixed but rotatable engagement therewith, e.g., via snap-fitting (see FIG. 9). Rotation knob 270, more specifically, defines a plurality of spaced-apart channels 276 arranged annularly about the interior surface that defines proximal portion 273 of lumen 272. Channels 276 each include a cam surface 277 on one side thereof, and a lock surface 278 on the other side thereof. Upon positioning of rotation knob 270 about torque housing 260, the free end of each cantilever arm 268 is received within one of channels 276. As detailed below, when rotation knob 270 is rotated in a first, or engaging direction, the free ends of cantilever arms 268 contact cam surfaces 277 of the respective channels 276 so as to impart corresponding rotation to torque housing 260 and, thus, waveguide 230. Upon meeting sufficient resistance to further rotation, cantilever arms 268 cam over cam surfaces 277 to decouple rotation knob 270 from torque housing 260 such that no further torqueing of torque housing 260 is permitted despite further rotation of rotation knob 270 (see FIG. 14). When rotation knob 270 is rotated in a second, opposite, or disengaging direction, the free ends of cantilever arms 268 contact lock surfaces 278 of the respective cannels 276 so as to impart corresponding rotation to torque housing 260 and, thus, waveguide 230, without limitation.

Turning to FIGS. 1, 2, 5, and 12-14, the assembly of ultrasonic surgical instrument 10 in preparation for use is detailed. Initially, with reference to FIG. 12, TAG 300 is engaged with body portion 112 of housing 110 of handle assembly 100 such that the appropriate contacts associated with TAG 300 are electrically coupled with the TAG contacts 142 of electrical connector 140 of housing 110. Thereafter, or prior to engagement of TAG 300, battery assembly 400 is aseptically transferred into and engaged within compartment 116 of fixed handle portion 114 of housing 110 of handle assembly 100 such that the appropriate contacts associated with battery assembly 400 are electrically coupled with battery assembly contacts 144 of electrical connector 140 of housing 110.

Next, as illustrated in FIGS. 2 and 13, elongated assembly 200, lead by proximal connector 236 of waveguide 230 is inserted proximally into handle assembly 100 until threaded male shaft 237 of proximal connector 236 is positioned adjacent threaded female receiver 326 of horn 324 of ultrasonic transducer 320. Once this position is achieved, the user grasps rotation knob 328 of ultrasonic transducer 320 with one hand, so as to stabilize and inhibit rotation of ultrasonic transducer 320, while grasping rotation knob 270 of elongated assembly 200 with the other hand. Rotation knob 270 of elongated assembly 200 is then rotated in the first, engagement direction, to threadingly engage threaded male shaft 237 of proximal connector 236 within threaded female receiver 326 of horn 324, hereby engaging waveguide 230 and ultrasonic transducer 320 with one another.

Figure 14:
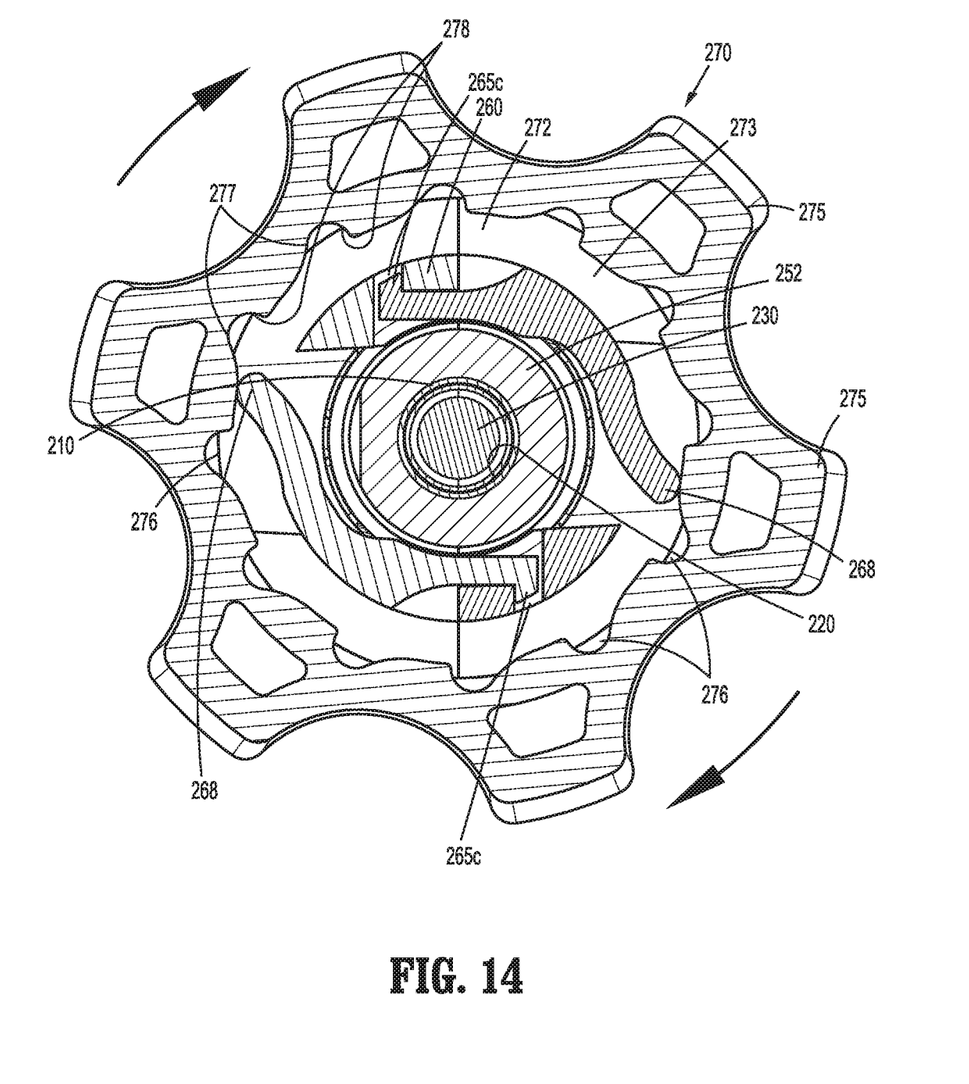
FIG. 14 is a transverse, cross-sectional view of the ultrasonic surgical instrument of FIG. 1 illustrating the torque-limiting action of the elongated assembly upon reaching a pre-defined torque during engagement of the elongated assembly with the handle assembly.

With additional reference to FIG. 14, rotation of rotation knob 270 is continued ultimately such that sufficient engagement between waveguide 230 and ultrasonic transducer 320 is achieved. At this point, further rotation of rotation knob 270 causes cantilever arms 268 of torque housing 260 to cam over cam surfaces 277 of rotation knob 270 such that rotation knob 270 rotates independently of torque housing 260. Upon cantilever arms 268 camming over cam surfaces 277 and out of channels 276, an audible and/or tactile "click" is produced. During engagement, rotation knob 270 may be rotated until two audible and/or tactile "clicks" are produced, thus ensuring that sufficient engagement of waveguide 230 and ultrasonic transducer 320 has been achieved.

Upon engagement of elongated assembly 200 with handle assembly 100, as detailed above and as illustrated in FIG. 13, elongated assembly 200 is positioned such that bifurcated drive portion 132 of clamp trigger 130 is disposed within annular gap 255 defined between the proximal end of ferrule 254 and raised collar 253a of drive tube 252, thereby operably coupling clamp trigger 130 with drive assembly 150.

Referring generally to FIG. 1, ultrasonic instrument 10, as assembled above, is now ready for use. In use, ultrasonic instrument 10 is inserted into and manipulated within a surgical site such that end effector 280 is positioned adjacent tissue to be treated. If needed, end effector 280 may be rotated relative to handle assembly 100 by rotating rotation knob 270 (without grasping rotation knob 328). Once positioned as desired, clamp trigger 130 may be actuated to pivot jaw member 282 from the open position towards the clamping position to clamp tissue to be treated between jaw member 282 and blade 234. As detailed above, drive assembly 250 functions to limit the clamping pressure applied to grasped tissue to a particular clamping pressure or a clamping pressure within a particular clamping pressure range.

With tissue sufficiently clamped between jaw member 282 and blade 234, activation button 120 may be activated in either the "LOW" power mode or the "HIGH" power mode to initiate the supply power from battery assembly 400 to TAG 300 for driving ultrasonic transducer 320 to, in turn, transmit ultrasonic mechanical motion along waveguide 230 to blade 234 for treating tissue therewith, in either the "LOW" power mode or the "HIGH" power mode.

Once tissue(s) is sufficiently treated, ultrasonic surgical instrument 10 is withdrawn from the surgical site. Thereafter, elongated assembly 200 is disengaged from handle assembly 100 by grasping rotation knob 328 of ultrasonic transducer 320 and rotating rotation knob 270 of elongated assembly 200 is the second, opposite, disengagement direction, to disengage proximal connector 236 of waveguide 230 from horn 324 of ultrasonic transducer 320. Once disengaged, elongated assembly 200 is removed from handle assembly 100 and discarded or sterilized for subsequent use.

With respect to handle assembly 100, TAG 300 is disengaged and removed therefrom for sterilization, and battery assembly 400 is removed and stored or placed on a charger (not shown) in preparation for subsequent use. Handle assembly 100 may then be discarded or sterilized for subsequent use.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An elongated assembly of an ultrasonic surgical instrument, the elongated assembly comprising:
   a waveguide including a torque adapter disposed thereabout towards a proximal end thereof;
   a drive assembly including a drive tube slidably disposed about the waveguide and receiving the torque adapter therethrough;
   a torque housing disposed about a portion of the drive tube and fixedly engaged about the torque adapter, wherein the drive tube is slidable through and relative to the torque housing; and
   a rotation knob longitudinally fixed about the torque housing and operably coupled to the torque housing such that the torque housing and the rotation knob cooperate to define a torque wrench configured to impart rotation to the waveguide in response to rotation of the rotation knob to facilitate engagement of the waveguide with an ultrasonic transducer up to a torque limit, and to decouple the rotation knob from the torque housing to inhibit application of additional torque to the waveguide above the torque limit.

2. The elongated assembly according to claim 1, wherein:
   the torque housing includes at least one cantilever arm extending outwardly therefrom; and
   the rotation knob defines a plurality of spaced-apart channels disposed radially about an annular interior surface thereof, wherein each of the at least one cantilever arms is configured for receipt within one of the plurality of spaced-apart channels to impart rotation to the waveguide in response to rotation of the rotation knob up to the torque limit, and wherein, each of the at least one cantilever arms is configured to cam out of the one of the plurality of spaced-apart channels to decouple the rotation knob from the torque housing to inhibit application of additional torque to the waveguide above the torque limit.

3. The elongated assembly according to claim 2, wherein the at least one cantilever arm includes a pair of opposed cantilever arms.

4. The elongated assembly according to claim 1, wherein the torque housing includes first and second housing parts configured to engage one another via snap-fitting to form the torque housing.

5. The elongated assembly according to claim 1, wherein the torque housing defines a receiver block configured to receive the torque adapter to fixedly engage the torque adapter and, thus, the waveguide relative to the torque housing.

6. The elongated assembly according to claim 1, wherein the drive assembly further includes a collar fixedly engaged about the drive tube, a washer fixed engaged about the drive tube towards at a position spaced-apart from the collar, a ferrule slidably disposed about the drive tube between the washer and the collar, and a spring disposed about the drive tube between the washer and the ferrule.

7. The elongated assembly according to claim 6, wherein the ferrule and the collar define an annular gap therebetween configured to receive a driving portion of a movable handle of an ultrasonic surgical instrument.

8. An ultrasonic surgical instrument, comprising:
a handle assembly including a housing and an ultrasonic transducer coupled to the housing; and
an elongated assembly configured for operable engagement with the handle assembly, the elongated assembly, including:
a waveguide including a torque adapter disposed thereabout towards a proximal end thereof;
a drive assembly including a drive tube slidably disposed about the waveguide and receiving the torque adapter therethrough;
a torque housing disposed about a portion of the drive tube and fixedly engaged about the torque adapter, wherein the drive tube is slidable through and relative to the torque housing; and
a rotation knob longitudinally fixed about the torque housing and operably coupled to the torque housing such that the torque housing and the rotation knob cooperate to define a torque wrench configured to impart rotation to the waveguide in response to rotation of the rotation knob to facilitate engagement of the waveguide with the ultrasonic transducer up to a torque limit, and to decouple the rotation knob from the torque housing to inhibit application of additional torque to the waveguide above the torque limit.

9. The ultrasonic surgical instrument according to claim 8, wherein the waveguide includes a first threaded connector and the transducer includes a second threaded connector, wherein the threaded connectors are configured to engage each other in response to rotation of the rotation knob.

10. The ultrasonic surgical instrument according to claim 8, further comprising a generator engaged with the ultrasonic transducer to define a transducer and generator assembly, the transducer and generator assembly configured to releasably couple to the housing.

11. The ultrasonic surgical instrument according to claim 10, further comprising a battery assembly configured to releasably couple to the housing, the battery assembly configured to power the generator for driving the ultrasonic transducer.

12. The ultrasonic surgical instrument according to claim 8, wherein the rotation knob is rotatably coupled to the housing.

13. The ultrasonic surgical instrument according to claim 8, wherein:
the torque housing includes at least one cantilever arm extending outwardly therefrom; and
the rotation knob defines a plurality of spaced-apart channels disposed radially about an annular interior surface thereof, wherein each of the at least one cantilever arms is configured for receipt within one of the plurality of spaced-apart channels to impart rotation to the waveguide in response to rotation of the rotation knob up to the torque limit, and wherein, each of the at least one cantilever arms is configured to cam out of the one of the plurality of spaced-apart channels to decouple the rotation knob from the torque housing to inhibit application of additional torque to the waveguide above the torque limit.

14. The ultrasonic surgical instrument according to claim 13, wherein the at least one cantilever arm includes a pair of opposed cantilever arms.

15. The ultrasonic surgical instrument according to claim 8, wherein the torque housing includes first and second housing parts configured to engage one another via snap-fitting to form the torque housing.

16. The ultrasonic surgical instrument according to claim 8, wherein the torque housing defines a receiver block configured to receive the torque adapter to fixedly engage the torque adapter and, thus, the waveguide relative to the torque housing.

17. The ultrasonic surgical instrument according to claim 8, wherein the drive assembly further includes a collar fixedly engaged about the drive tube, a washer fixed engaged about the drive tube towards at a position spaced-apart from the collar, a ferrule slidably disposed about the drive tube between the washer and the collar, and a spring disposed about the drive tube between the washer and the ferrule.

18. The ultrasonic surgical instrument according to claim 17, wherein the ferrule and the collar define an annular gap therebetween configured to receive a driving portion of a movable handle of the handle assembly.

* * * * *